United States Patent [19]

Leister et al.

[11] 3,994,958

[45] Nov. 30, 1976

[54] POST REACTED OLIGOMERS

[75] Inventors: Norman A. Leister, Huntingdon Valley; Richard J. Piccolini, Newtown, both of Pa.

[73] Assignee: Rohm and Haas Company, Philadelphia, Pa.

[22] Filed: June 12, 1975

[21] Appl. No.: 586,476

Related U.S. Application Data

[62] Division of Ser. No. 180,142, Sept. 13, 1971, Pat. No. 3,968,148.

[52] U.S. Cl. ............................................ 260/482 P
[51] Int. Cl.² ...................................... C07C 103/44
[58] Field of Search ................................. 260/482 P

[56] References Cited
UNITED STATES PATENTS 3,803,254   4/1974   Hattori et al. .................... 260/669 P

*Primary Examiner*—Robert Gerstl

[57] ABSTRACT

This invention relates to novel oligomers of 1-alkenes and derivatives of acrylic acids, to methods of making the oligomers, and to compositions which comprise the oligomers.

1 Claim, No Drawings

POST REACTED OLIGOMERS

This application is a divisional application of our earlier copending application, Ser. No. 180,142, filed Sept. 13, 1971, and entitled "Copolymers of 1-Alkenes and Acrylic Acid Derivatives and Method of Making Same" now U.S. Pat. No. 3,968,148.

BACKGROUND OF THE INVENTION

The known techniques for preparing 1-alkene containing copolymers yield products which have a wide molecular weight diversity and an extreme compositional heterogeneity. While the copolymers formed may display some beneficial properties, the overall effect of using a given amount of the polymer will be diminished by that part of the product having a molecular weight or composition which possesses detrimental or non-useful qualtities. Thus, in order to produce a polymer in which the good qualities are concentrated so that less of the polymer need be used to accomplish a desired effect, it would be desirable to employ a polymerization technique which would allow for such control of polymer molecular weight and composition so that most of the polymeric material produced would have the beneficial qualities sought.

The prior art discloses a series of amide-containing copolymers which are disclosed as useful as additives to oil, to wit, Bondi 2,800,452 (filed July 1954), and Newey 2,912,416 (also filed July 1954). They do not, however, teach or suggest the presently disclosed 1-alkenesalkyl acrylates higher alkyl acrylate oligomers, which have superior sludge dispersant properties.

The '416 patent recites an amide-containing copolymer based on components which cannot produce the presently taught oligomers.

Similarly, the '452 patent does not include the higher alkyl acrylate components of the type contemplated for use in the presently taught oligomers; rather, it intended to exclude long chain esters, which we have discovered contribute significantly to the here-desired oil-solubility and/or dispersancy of the resulting oligomer.

Indeed, it can fairly be said that the cited patents actually lead away from using higher alkyl acrylates, in view of their statements that such components are undesirably hydrolytically unstable.

THE INVENTION

Accordingly, it is an object of the invention to provide a novel process for making oligomers.

Another object of the invention is to provide novel oligomers and oligomeric products comprising these oligomers.

A further object of the invention is to provide novel oligomers containing 1-alkenes and higher alkyl derivatives of acrylic acids and having a narrow range of molecular weight and high compositional homogeneity.

Still another object of the invention is to provide novel additives for lubricating oils which are useful as low temperature and ashless sludge dispersants and detergents. These and other objects will be apparent from the specification and claims.

It has now been found that these and other objects may be accomplished by oligomers which are produced by an oligomerization process which comprises the continuous addition of at least one derivative of an acrylic acid to a mixture of a free radical initiator and at least one alkene-1 having 4 to 32 carbon atoms or more, in which the addition is carried out at such a rate that the substantially instantaneous mole ratio in the reaction mixture of the derivative to the alkene-1 is maintained relatively constant at from about 0.01 to about 0.20 during the addition. At a given reaction temperature and catalyst concentration, the molecular weight of the oligomer produced will be directly related to the mole ratio of the acrylic acid derivative(s) to the alkene-1. Varying this mole ratio between 0.01 and 0.20 will give oligomers having a degree of polymerization of about 4 to about 35.

When the resulting oligomeric products of the invention are added to lubricating oils, they show activity as low temperature sludge dispersants and as detergents. Since oligomers produced by the process of the invention have relatively uniform molecular weight and composition, the effect of a given amount of the oligomer as a sludge dispersant or detergent can be heightened by suitable control of molecular weight and composition.

One of the advantages of the invention is that the molecular weight of the oligomer can be controlled, to give a product having a molecular weight falling within a narrow range, by adjusting the rate of addition of the acrylic derivative, in order to maintain a specified mole ratio of acrylic derivative to alkene-1 in the reaction mixture.

In producing the compounds which are useful as additives to lubricating oils, the oligomers of the invention may be post-reacted with alcohols, esters, or amines to form new oligomeric products. Among the post-reactions which are especially useful are the reaction of an ester of an acrylic acid with an alcohol to give a new acrylic ester through transesterification or with an amine to give an acrylic amide through aminolysis, the reaction of an acrylic acid with an alcohol to give an acrylic ester, and the reaction of an alkyl nitrile with an ethylenediamine to give an imidazoline.

Furthermore, a third monomer co-oligomerizable with the acrylic acid derivative and the alkene-1 may be added prior to the addition process, either to the acrylic derivative or to the alkene-1, thus forming a co-oligomer of the acrylic derivative, alkene-1 and said third monomer. Both of the above variations in the polymerization process of the invention are useful for introducing valuable modifications into the oligomers of the invention.

The novel oligomers of the invention are oligomers of:

a. about 10 to 90% by weight of a 1-alkene or a mixture of 1-alkenes;

b. about 1 to 45% by weight of a straight or branched chain alkyl acrylate or methacrylate in which the alkyl group contains 8 to 34 carbon atoms, and;

c. 1 to about 35% by weight of an acrylic acid, ester or nitrile, or an amide or an amino derivative of an acrylic acid, or a mixture of such acids, esters, nitriles, and amido and amino derivatives.

The first component of the oligomers of the invention is an olefin of the following Formula I:

wherein $R_1$ is alkyl, and $R_2$ is H or alkyl.

Any polymerizable terminal olefin having 4 to 32 carbon atoms or more which will oligomerize with one of the acrylic acid derivatives can be used in the oligomerization process of the invention. Mixtures of such alkenes can also be used.

Among the purposes of the alkene-1 are the following: to confer a high degree of oil-solubility upon the oligomer, as well as close control over the molecular weight. Examples of such oligomerizable olefins desirable for this purpose include: butene-1, pentene-1, hexene-1, heptene-1, octene-1, nonene-1, decene-1, undecene-1, dodecene-1, tridecene-1, tetradecene-1, pentadecene-1, hexadecene-1, heptadecene-1, octadecene-1, nonoadecene-1, eicosene-1, heneicosene-1, docosene-1, tricosene-1, tetradosene-1, pentacosene-1, hexacosene-1, heptacosene-1, octacosene-1, nonacosene-1, triacontene-1, hentriacontene-1, dotriacontene-1, and the like. Also useful are branched-chain alkenes such as vinylcyclohexane, 3,3-dimethylbutene-1, 3-methylbutene-1, diisobutylene 4-methylpentene-1, and the like.

Likewise useful in this invention are alkene-1's having 10 to 32 carbon atoms, derived from the polymerization of ethylene, propylene, or mixtures thereof, which in turn are commercially provided from hydrocracked stocks.

The second component of the oligomers of the invention is an acrylic ester of the following formula II:

where X is hydrogen or methyl, and R is a straight or branched chain alkyl group having 8 to 34 carbon atoms.

Mixtures of the compounds of formula II can also be used. Examples of such compounds include: 2-ethylhexyl acrylate, isodecyl acrylate, decyl acrylate, undecyl acrylate, dodecyl acrylate, tridecyl acrylate, tetradecyl acrylate, pentadecyl acrylate, dodecyl-pentadecyl acrylate, hexadecyl acrylate, heptadecyl acrylate, octadecyl acrylate, cetylstearyl acrylate, oleyl acrylate, nonadecyl acrylate, eicosyl acrylate, cetyl-eicosyl acrylate, stearyl-eicosyl acrylate, docosyl acrylate, eicosyl-tetratriacontyl acrylate, and the like.

The third component of the oligomers of the invention is a compound of the following formula III:

wherein
$R_1$ may be H, $CO_2H$ or $CO_2R_4$ ($R_4$ is an alkyl group having 1 to 4 carbon atoms);
$R_2$ is $(CH_2)_n$ X, wherein $n$ is an integer ranging in value from 0 to 8, and
$R_3$ is hydrogen or methyl.
X may be halogen, $-CO_2H$, $-C \equiv N$, $-CO_2R_5$ ($R_5$ may be any alkyl group having 1 to 4 carbon atoms or it may be a polar moiety containing ether or sulfide or sulfinyl or hydroxyl or amine or amide groups or combinations thereof and the like, (containing as many as 12 carbon atoms), or

(Y is one of $-NZ'Z''$, $-O(CH_2)_n NZ'Z''$, $\equiv -O(CH_2)_n CONZ'Z''$, $-NHNZ'N''$ or $-N^-N^+Z_3''$ wherein $n$ is a whole positive integer from 1 to 12, $Z'$ is hydrogen or an alkyl group straight or branched of 1 to 20 carbon atoms,
$Z''$ is hydrogen or an alkyl group of 1 to 20 carbon atoms
$Z'''$ is an alkyl group of 1 to 4 carbon atoms, and
$Z'$ and $Z''$ can be taken together to form an azacycloalkyl ring, an azacycloalkanone ring, a carbalkoxyazacycloalkanone ring, an oxaazacycloalkyl ring, an oxaazacycloalkanone ring or a diazacycloalkanone ring);
X may also be N-pyrrolidinyl and the like;
$R_1$ and $R_2$ together may be an anhydride group.

Among the compounds of formula III are acrylic acid, methacrylic acids or derivatives thereof. Also included are suitably substituted polymerizable olefins which may be used to introduce into the oligomer functional groups to be subsequently transformed into dispersant sites by reaction with amines and polyamines, esters, alcohols and aminoalcohols, or which may be derivatized with these compounds.

Examples of such substituted oligomerizable olefins include: 4-chlorobutene-1, 4-pentenonitrile, 4-pentenoic acid, methyl 4-pentenoate, ethyl 4-pentenoate, 5-hexenoic acid, 6-bromohexene-1, 10-undecenoic acid, methyl 10-undecenoate, and ethyl 10-undecenoate, and 4-pentenamides.

Mixtures of the compounds of Formula III may also be used. Examples of such compounds include: acrylic acid, methacrylic acid, methyl acrylate, methyl methacrylate, methyl chloracrylate, ethyl acrylate, propyl acrylate, n-butyl acrylate, acrylonitrile, 1-(methacryloxyethyl)-2-pyrrolidinone, 1-(methacryloxyethoxyethyl)-2-pyrrolidinone, and the like.

Other examples are methylthioalkyl acrylate (alkylene group is $C_{1-9}$), ethylthioalkyl acrylate (alkylene group is $C_{1-8}$), alkylthioethyl acrylate (alkyl group is $C_{1-8}$) and alkylsulfinylalkyl acrylates, in which the alkyl and alkylene groups together contain no more than ten carbon atoms, alkylthiopolyethoxyethyl acrylates containing one to four oxyethylene groups, alkylthiopolypropyloxypropyl acrylates containing one to three oxypropylene groups, alkylsulfinylpolyethoxyethyl acrylates containing one to four oxyethylene groups, alkylsulfinylpolypropyloxypropyl acrylates containing one to three oxypropylene groups (in each of the foregoing, the total number of carbon atoms of $R_5$ group is no more than ten), and the like.

Other examples of such derivatives include methacrylamide, acrylamide, N-methylacrylamide, N-ethylacrylamide, N-ethylacrylamide, N-butanolacrylamide, 2-(N-morpholino) ethyl acrylamide, N,N-dimethylacrylamide, N,N-diethylacrylamide, N-t-butylacrylamide, N,N-di-n-butylacrylamide, N-(2-acryloxyethyl)-morpholinone-2-, N-(2-methacryloxyethyl)-morpholinone-2, N-(2-methacryloxyethyl)-5-carbo-n-butoxypiperidinone-2, 2-(N,N dimethylamino) ethyl acrylate, 3-(N,N-dimethylamino) propyl acrylate, 2-(N-t-butylamino) ethyl acrylate, 2-(N,N-dimethyl-amino) ethyl methacrylate, and 3-(N,N-dimethylamino)propyl methacrylate.

Two processes can be used in producing the oligomers of the invention. The first process comprises the continuous addition of at least one compound of Formula I and II, to at least one compound of Formula III that is already a dispersant monomer.

The addition is carried out at such a rate that the substantially instantaneous mole ratio in the reaction mixture of compounds of Formulas II and III to compounds of Formula I is maintained relatively constant at from about 0.01 to about 0.20 during the addition. A free radical initiator is mixed with the Formula II compound, or Formula I compound, or both, prior to the addition.

In the second process for producing the oligomer of the invention, an oligomer produced by the continuous addition of at least one compound of Formulas II and III to at least one compound of Formula I, by a process similar to that described above, is post-reacted with an alcohol or an amine. Thus, when an acrylic acid or an acrylic ester is used as a starting monomer (that is, when $R_1$ is H and $R_2$ is $-CO_2H$ or $-CO_2R_4$ in Formula III,) or when a substituted 1-olefin bearing an acid or ester group is employed, the acid groups or the ester groups in the oligomer can be post-reacted with an alcohol or an amine having the formula HZ'''; wherein Z''' is as defined in Formula III, or these groups can be neutralized or hydrolyzed with a base to form a salt of an acrylic acid. The relative amounts of the reactants can be chosen so that any desired percentage of the acid or ester groups can be converted to the desired derivative.

Among the alcohols and amines which may be post-reacted with the acid or ester groups in the oligomer are N-hydroxyethylmorpholinone-2, N-hydroxyethylpyrrlidone, N,N-dimethylaminoethylamine, 5-aminopentylimidazoline, diethylenetriamine, aminoethylethylene urea, 2-(2-aminoethyl)-aminoethanol, triethylenetramine, tetraethylenepentamine and N,N-dimethylaminopropylamine.

Besides these useful post-reactions we have found the reaction of multifunctional alcohols and amines with carboxylic acid groups present in oligomers (to form esters, or amides or amine salts) to be a most effective way of introducing into the oligomers polar groups with detergents, dispersant and/or anti-oxidant activity. The carboxylic acid groups may be provided, for example, by the use of acrylic acid, 4-pentenoic acid or 10-undecenoic acid as monomers.

Such alcohols and amines include ethylene glycol, diethylene glycol, triethylene glycol, glycerol, sorbitol, erythritol, trimethylene glycol, pentaerythritol, $C_{4-12}$-alkyl glucosides, alkylthioalkanols and alkylsulfinylalkanols, where the alkyl and alkylene groups have one to 12 carbons, 2,2'-thiodiethanol, 2,2'-sulfinyldiethanol, diethanolamine, triethanolamine, N-methyldiethanolamine, diglycolamine, N-methylformamide, glucosylamine, N-(B-hydroxyethyl)-morpholine, N-(B-hydroxyethyl)-morpholinone, 2-(2-aminoethylamino)-ethanol, N-(2-hydroxyethyl)-piperazine, 1-(B-hydroxyethyl)-2-pyrrolidinone, )-(hydroxyethoxyethyl)-2-pyrrolidinone, N,N-dimethylaminopropylamine, N-(2-aminoethyl)-ethyleneurea, N-(2-aminoethyl)-piperazine, calcium N-methyltaurate, ethylenediamine, diethylenetriamine, triethylenetetramine, tetraethylenepentamine and pentaethylenehexamine.

Also, oligomeric carboxylic acids or their methyl or ethyl esters, having been post-reacted with diethylene triamine, triethylenetetramine, tetraethylenepentamine, pentaethylenehexamine, etc., may be further reacted with one to five equivalents of methyl or ethyl formate, methyl or ethyl acetate, ethylene oxide or propylene oxide, phosphorus pentasulfide, carbon disulfide, acrylo-or acetonitrile giving corresponding formamides, acetamides, hydroxyethyl or hydroxypropyl, thiophosphoramide, thiocarbamate 2-cyanoethyl or imidazoline derivatives.

Any suitable catalyst may be used in the production of the copolymers of the invention. Among the preferred catalysts are peroxide catalysts, such as, for example, benzoyl peroxide, lauroyl peroxide, tertiary butyl hydroperoxide, cumene hydroperoxide, 2,2-bis-(tertiary butylperoxy)-butane, di-(tertiary butyl) peroxide tertiary butyl perpelargonate, tertiary-butyl perbenzoate, hydrogen peroxide, and percarbonates, peracetic acid, and the like. The amount of catalyst which is added will vary, depending on the monomers employed as starting materials, reaction temperature, degree of polymerization desired, etc., but generally the catalyst will be present at about 0.01 to 10% by weight of the material being polymerized, and preferably will be present at about 0.1 to 1.0 percent by weight.

The temperature at which the oligomerization reaction is run can also be varied over a broad range, and any temperature which will not impair the oligomerization can be selected. A preferred reaction temperature range is from about 100° C. to 200° C. While the choice of catalyst and reaction temperature may be used to exert some control over the molecular weight of the oligomers produced according to the invention, the major factor which determines the copolymer molecular weight is the mole ratio of the acrylic acid derivative to the alkene-1, as described above.

In a preferred embodiment of the invention, the alkene-1 mixture and the acrylic acid derivatives will contain an alkyl chain of sufficient average length to impart oil-solubility to the oligomer. Among the monomers which are particularly useful in making oil-soluble oligomer are those having alkyl chains averaging 8 atoms or more, such as tetradecene-1, n-dodecyl acrylate, and the like.

When the oligomeric products of the invention are added to lubricating oils, they show activity as low temperature sludge dispersants and as detergents. Since oligomers produced by the process of the invention have relatively uniform molecular weight and composition, the effect of a given amount of the polymer as a sludge dispersant or detergent can be heightened by suitable control of molecular weight and composition.

One of the advantages of the invention is that the molecular weight of the oligomer can be controlled, to give a product having a molecular weight falling within a narrow range of distribution, by adjusting the rate of addition of the acrylic derivative in order to maintain a specified mole ratio of acrylic derivative to alkene-1 in the reaction mixture.

The following working examples illustrate systheses within the teaching of the present invention which may be employed in formulating the compositions of the invention but are not considered limiting the invention described heretofore.

EXAMPLE I

Preparation of Oligomer: HD/DPA/AA/58.3/21.1/20/6

Into a 12-liter, 3-necked, round-bottom flask fitted with a motor-driven C-stirrer, thermometer, reflux condenser and a 1000-ml. graduated dropping addition funnel is added 6207 g. (27.66 moles) of 1-hexadecene (HD) from Gulf Oil Corporation. The alkene is heated with stirring in a nitrogen atmosphere to 132° and 7.30 g. (0.0319 mole) of 85% t-butyl perbenzoate in xylene is added rapidly. A total of 497.7 g. (2.28 moles) of dodecyl-pentadecyl acrylate (DPA), 694.0 g. (9.63 moles) of acrylic acid (AA), and 4.44 g. (0.0194 moles) of 85% t-butyl perbenzoate is blended and charged to the dropping addition funnel; and addition of acrylate/acrylic acid is carried out at a constant rate for 6.38 hours. The pot temperature is maintained at 132°–135° with moderate stirring for 16 hours. The temperature is then raised to 192°, and unreacted monomers are distilled under gradually reduced pressure to 1 mm. Hg. After 45 minutes at 192°/1 mm. Hg. the residue is cooled to 130° and weighed. After a sample had been removed for analysis, the remaining oligomer was diluted to a 52.0% solution with 100 neutral oil in order to confer acceptable fluidity upon the product.

In a typical preparation, the amount of oligomer produced was 3001.5 g. (a 40.0% yield); it was found to have the composition HD/DPA/AA/58.3/21.1/20.6 and a number-average molecular weight of 3200 ± 10.

EXAMPLE IIA

Preparation of the Oligomer: TD/DPA/AA//49.7/27.8/22.5

A 12-liter, 3-necked, round-bottom flask is charged with 5265 g. (26.8 moles) of commercial tetradecene (92-93% 1-tetradecene) and is then fitted with a motor-driven Trubore C-stirrer, a candlestick adapter holding a thermometer and a 1-liter graduated dropping addition funnel, and a reflux condenser. The alkene is heated with stirring in an atmosphere of nitrogen to 132° C. A total of 6.20 g. of t-butyl perbenzoate is added directly and five minutes later the continuous addition of a solution of 1310 g. (5.00 moles) of dodecylpentadecyl acrylate, 1035 g. (14.36 moles) of acrylic acid and 8.28 g. of t-butyl perbenzoate is begun via the dropping addition funnel. With the reaction temperature maintained at 132°-133°, the addition of acrylate solution is completed in 4.75 hours; the product mixture is held at 132° (with stirring) for 16 hours. The temperature is then raised to 192° and unreacted monomers are distilled under gradually reduced pressure to 1 mm. Hg. pressure. After 45 minutes at 192°/1 mm. Hg., the residue is cooled to 135° and weighed. After a sample of oligomer has been removed for analysis, the remainder is diluted to 55% with 100 neutral oil to give a product with acceptable fluidity at room temperature.

In a typical preparation, the weight of oligomer produced was 4458 g. (a 58.6% yield); it was found to have the composition TD/DPA/AA//49.7/27.8/22.5 and a number-average molecular weight of 4240 ± 10, and diluted to a 52.0% solution with 100 neutral oil.

EXAMPLE IIB

The Esterification of TD/DPA/AA//49.7/27.8/22.5; ($\overline{M}_n = 4240 \pm 10$) with 2,2'-Sulfinyldiethanol To a 2-liter, 3-necked round-bottom flask fitted with a motor-driven C-stirrer, thermometer and a Dean-Stark trap connected to an Allihn condenser, are added 477.3 g. (0.8027 equiv., based on AA) of a 52.0% solution of the TD/DPA/AA oligomer of Ex. IIA in 100 neutral oil, 138.2 g. (1.00 mole) of 2,2'-sulfinyldiethanol and 400 ml. of xylene. The mixture is heated under gentle reflux (152°–153°) with moderate stirring for 6 hours, with water removed as it formed.

The product mixture is cooled to 105° and diluted with 272.2 g. of 100 neutral oil. Xylene is removed by strip-distillation to 150°/2 mm. Hg. The product and unreacted 2,2'-sulfinyldiethanol are partitioned between hexane and 16% aqueous magnesium sulfate solution. Water is removed from the solution of product by azeotropic distillation and hexane is removed by strip-distillation to 135°/2 mm. Hg. Analysis of a typical product indicated that the extent of esterification was 37%.

A reaction product of the above ester and 2,2'-sulfinyldiethanol, in which 43% esterification was achieved, attained a sludge rating of 37.2 (50.0 = clean), and a varnish rating of 33.6 (50.0 = clean) in the MS Sequence V-B test after 192 hours.

EXAMPLE III

The preparation of HD/DPA/AA//59.8/24.0/16.2

To a 12-liter, 3-necked, round-bottom flask fitted with a motor-driven C-stirrer, thermometer, reflux condenser and two graduated dropping addition funnels is added 3250.0 g. (14.48 moles) of 1-hexadecene. The alkene is heated with stirring in a nitrogen atmosphere to 164° and a mixture of 14.9 g. (0.057 mole) of dodecyl-pentadecyl acrylate, 9.1 g. (0.13 mole) of acrylic acid and 4.5 g. (0.022 mole) of dodecyl mercaptan is added rapidly. To one addition funnel is charged a mixture of 445.0 g. (1.70 moles) of dodecyl-pentadecyl acrylate and 286.0 g. (3.97 moles) of acrylic acid, and to the other addition funnel is added a 400.0 g. (1.78 moles) of 1-hexadecene and 7.6 g. (0.033 mole) of 85% t-butyl perbenzoate in xylene. The contents of each addition funnel are added simultaneously at a constant rate over 7.54 hours with the pot temperature maintained at 160°–164°.

Upon completion of addition of acrylate/acrylic acid and solution of initiator the reaction mixture is allowed to cool with stirring to 132° overnight (16 hours). The temperature is then raised to 192° and unreacted monomers are distilled under gradually reduced pressure to 1 mm. Hg. After 45 minutes at 192°/1 mm. Hg. the residue is cooled to 135° and diluted to a 54.9% solution with 100 neutral oil.

In a typical preparation, the weight of oligomer produced was 1728.3 g. (a 39.2% yield). It was found to have the composition HD/DPA/AA//59.8/24.0/16.2 and a number-average molecular weight of 2030 ± 20.

EXAMPLE IV

Synthesis of the Oligomer: HD/DPA/MU//22.5/58.2/19.3

Into a 12-liter, 3-necked, round-bottom flask fitted with a motor-driven Trubore C-stirrer, thermometer, reflux condenser and 1-liter graduated dropping addition funnel are charged 2074.2 g. (9.242 moles) of 1-hexadecene and 1319.9 g. (6.656 moles) of methyl 10-undecenoate (MU). The alkene mixture is heated with stirring to 132° in a nitrogen atmosphere and 5.0 g. (0.022 mole) of 85% t-butyl perbenzoate in xylene is added. A total of 1972.0 g. (7.527 moles) of dodecyl-pentadecyl acrylate and 7.0 g. (0.031 mole) of 85% t-butyl perbenzoate are charged to the dropping addition funnel; and addition of acrylate is carried out at a constant rate over 6.13 hours with the pot temperature maintained at 132°–135°.

Upon completion of addition of acrylate, heating is continued at 132°–134° with moderate stirring for 16 hours. The pot temperature is then raised to 193° and unreacted monomers are distilled under gradually reduced pressure to 2 mm. Hg. After 45 minutes at 193°/2 mm. Hg. the residue is cooled to room temperature in a nitrogen atmosphere.

In a typical preparation, the weight of product was 3121.9 g. (a 58.2% yield). The oligomer was found to have the composition HD/DPA/MU//22.5/58.2/19.3 with a number-average molecular weight of 3020 ± 15.

EXAMPLE V

Synthesis of the Oligomer: HD/DPA/MP//27.9/62.0/10.1

Into a 12-liter, 3-necked, round-bottom flask fitted with a motor-driven Trubore C-stirrer, thermometer, reflux condenser and 1-liter graduated dropping addition funnel are charged 2468.8 g. (11.00 moles) of 1-hexadecene and 1009.3 g. (8.842 moles) of methyl 4-pentenoate (MP). The alkene mixture is heated with stirring continued 132°, in a nitrogen atmosphere, and 5.11 g. (0.0224 mole) of 85% t-butyl perbenzoate in xylene is added. A total of 2206.0 g. (8.420 moles) of dodecyl-pentadecyl acrylate and 7.79 g. (0.0341 mole) of 85% t-butyl perbenzoate are charged to the dropping addition funnel; and addition of acrylate is carried out at a constant rate over 8.25 hours with the pot temperature maintained at 132°–134°. Upon completion of addition of acrylate, heating is continuaned at 132°–134° with moderate stirring for 15 hours. The pot temperature is then raised to 192° and unreacted monomers are distilled under gradually reduced pressure to 1 mm. Hg. After 45 minutes at 192°/1 mm. Hg. the residue is cooled to room temperature in a nitrogen atmosphere.

In a typical preparation, the weight of product was 3556.7 g. (a 62.6% yield). The oligomer was found to have the composition HD/DPA/MP//27.9/62.0/10.1 with a number-average molecular weight of 2875 ± 75.

EXAMPLE VI

The Reaction of the Oligomer of Example V with Diethylenetriamine

To a 2-liter, 3-necked, round-bottom flask fitted with a motor-driven Trubore C-stirrer, thermometer and reflux-distillation head are added 400.0 g. (0.347 equiv., based on MP) of the oligomer of Ex. V and 62.0 g. (0.601 mole) of technical-grade diethylenetriamine. The reaction mixture is heated with moderate stirring at 150°–155° for 6 hours in a nitrogen atmosphere and methanol is removed as formed. The product mixture is diluted with 400.0 g. of 100 neutral oil and unreacted amine is strip-distilled at 155° with the pressure gradually reduced to 3 mm. Hg.

The product is cooled to room temperature in an atmosphere of nitrogen. In a typical preparation, a total of 802 g. of product, containing 1.52% nitrogen, was recovered. Analytical data indicated that 73.9% of the carbomethoxy groups from MP had been amidated.

This material attained a sludge rating of 35.0 (50.0 = clean) and a varnish rating of 37.8 (50.0 = clean) in the MS Sequence V-B test (see ASTM Special Technical Publication No. 315-D) test after 192 hours. Under similar test conditions OLOA 1200 (a polybutane-based succinimide) a commercial product marketed by Socal, Oronite Division, achieved a sludge rating of 35.1 and a varnish rating of 31.2.

EXAMPLE VII

The Synthesis of the Oligomer: HD/DPA/MA//52.1/39.7/8.2

To a 2-liter, 3-necked, round-bottom flask fitted with a motor-driven Trubore C-stirrer, thermometer, reflux condenser, 125-ml. graduated dropping addition funnel and a 250 ml. graduated dropping addition funnel is added 589.6 g. (2.627 moles) of 1-hexadecene. The alkene is heated in a nitrogen atmosphere at 185° with moderate stirring. A total of 1.615 g. (0.0106 mole) of cumene hydroperoxide in 6.01 g. (0.022 mole) of 1-hexadecene is added rapidly. Seventeen minutes later the simultaneous but separate additions of a solution of 245.0 g. (0.935 mole) of dodecyl-pentadecyl acrylate and 65.3 g. (0.763 mole) of methyl acrylate (MA) and a solution of 1.256 g. (0.00825 mole) of cumene hydroperoxide in 25.0 g. (0.111 mole) of 1-hexadecene are begun.

The continuous additions of monomers and initiator are carried out at a constant rate, so that after 7.06 hours the addition of acrylate monomers is complete, while that of initiator is 97% complete. The remaining initiator is added rapidly and the reaction mixture is allowed to cool to 132° over the space of 16 hours with moderate stirring. The product mixture is heated at 190° for 1.5 hours with moderate stirring in a nitrogen atmosphere and then unreacted monomers are removed by strip-distillation at 190° with the pressure gradually reduced to 3.5 mm. Hg. The residue is then cooled to 60° in a nitrogen atmosphere and clarified by filtration.

In a typical preparation, the weight of product was 608.8 g. (a 65.4% yield); the oligomer was found to have the composition HD/DPA//MA//52.1/39.7/8.2 with a number-average molecular weight of 1625 ± 10.

EXAMPLE VIII

The Reaction of the Oligomer: HD/DPA/MA//51.8/38.1/10.1 with Triethylenetetramine To a 3-liter, 3-necked, round-bottom flask fitted with a motor-driven Trubore C-stirrer, thermometer and reflux-distillation head are added 350.0 g. (0.4102 equiv., based on MA) of the oligomer and 73.2 g. (0.501 mole) of triethylenetetramine. The mixture is heated at 140° with moderate stirring in a nitrogen atmosphere for 8 hours. It is then cooled to 120° and diluted with 350.0 g. of 100 neutral oil, 300 ml. of toluene and 300 ml. of isobutyl alcohol. A total of 100.0 g. (0.350 equiv. H$^+$) of Amberlyst 15 resin beads is added and the mixture is stirred slowly overnight at ambient temperature. The mixture is then stirred in a nitrogen atmosphere at 85° for 1 hour and is cooled and filtered. Solvents and traces of unsequestered triethylenetetramine are removed by strip-distillation to 125° with the pressure gradually reduced to 1.5 mm. Hg. The product is cooled in an atmosphere of nitrogen.

In a typical preparation the product, which had a base number of 47.4 and contained 1.68% nitrogen, was amidated at 48.7% of the carbomethoxy groups from MA and 3.6% of the carboalkoxy groups from DPA. This material attained a sludge rating of 36.2 (50.0 = clean) and a varnish rating of 32.1 (50.0 = clean) in the MS Sequence V-B test after 192 hours.

Under similar test conditions, OLOA-1200 a commercial product (a polybutene-based succinimide) marketed by Socal, Oronite Division, achieved a sludge rating of 35.1 and a varnish rating of 31.2.

EXAMPLE IX

The Reaction of Ethyl Formate with the Oligomer HD/DPA/MA//50.3/39.8/9.9 Previously Condensed with Triethylenetetramine To a 2-liter, 3-necked, round-bottom flask fitted with a motor-driven Trubore C-stirrer, thermometer, reflux-distillation head and 125 ml. dropping addition funnel is added 771.7 g. (0.486 equiv. of primary amine) of the amidated oligomer. This material is the condensation product of the oligomer (HD/DPA/MA//50.3/39.8/9.9; $\overline{M}_n = 1745 \pm 15$) and triethylenetetramine, in which 45.4% of the carbomethoxy groups from MA and 19.6% of the carboalkoxy groups from DPA had been amidated. The oligomer is heated with moderate stirring to 88° in an atmosphere of nitrogen, and 42.4 g. (0.572 mole) of ethyl formate is added dropwise over the space of 10 minutes. Heating is continued at 88° for 2 hours. Volatile material is stripped at 90° with the pressure gradually reduced to 1 mm. Hg. The product is then cooled in an atmosphere of nitrogen. In a typical preparation, a total of 0.432 equiv. of amine are formulated.

A formulated oil containing 1.20% of this product as the sludge dispersant showed 11% top-groove fill after 240 hours in the Caterpillar 1-H test. The same oil lacking a dispersant showed 36% top-groove fill after 240 hours.

EXAMPLE X

The Synthesis of the Oligomer: HD/CEA/MA//48.7/41.7/9.6

To a 3-liter, 3-necked, round-bottom flask fitted with a motor-driven Trubore C-stirrer, thermometer, reflux condenser, 125-ml. graduated dropping addition funnel and a 1-liter graduated dropping addition funnel are added 901.3 g. (4.016 moles) of 1-hexadecene. The alkene is heated in a nitrogen atmosphere at 185° with moderate stirring. A total of 0.90 g. (0.0059 mole) of cumene hydroperoxide in 10.0 g. of tridecane is added rapidly. Ten minutes later the simultaneous but separate additions of a solution of 280.0 g. (0.8578 mole) of cetyl-eicosyl acrylate (CEA) and 77.4 g. (0.899 mole) of methylacrylate and 2.5 gm. of cumene hydroperoxide in 50.0 g. of tridecane are begun. The continuous additions of monomers and initiator proceeds at a constant rate and is completed after 6.93 hours.

The reaction mixture is allowed to cool to 132° over the space of 17 hours with moderate stirring. The product mixture is then heated to 192° and unreacted monomers are removed by strip-distillation at 193° with the pressure gradually reduced to 3 mm Hg. The residue is cooled to room temperature in an atmosphere of nitrogen and is clarified by filtration.

In a typical preparation, the weight of product was 662.9 g. (a 52.7% yield); the oligomer was found to have the composition HD/CEA/MA//48.7/41.7/9.6 with a number-average molecular weight of $1425 \pm 25$.

EXAMPLE XI

The Synthesis of the Oligomer: OD/DPA/MA//65.0/14.3/20.7

To a 5-liter, 3-necked, round-bottom flask fitted with a motor-driven Trubore C-stirrer, thermometer, reflux condenser, 125 ml. graduated dropping addition funnel and a 1-liter graduated dropping addition funnel is added 2424.9 g. (9.604 moles) of 1-octadecene. The alkene is heated at 185° with moderate stirring in a nitrogen atmosphere. A total of 0.8169 g. (0.00537 mole) of cumene hydroperoxide in 25.0 g. (0.099 mole) of 1-octadecene is added rapidly. Seventeen minutes later the simultaneous but separate additions of a solution of 262.0 g. (1.00 mole) of dodecylpentadecyl acrylate, and 416.6 g. (4.737 moles) of methyl acrylate, and a solution of 4.5322 g. (0.02978 mole) of cumene hydroperoxide in 75.0 g. (0.297 mole) of 1-octadecene are begun.

The continuous addition of monomers and initiator proceeds at a constant rate and after 7 hours the addition of acrylate monomers is complete, while that of initiator is 93.3% complete. The remaining initiator is added rapidly and heating at 185° is continued for 1 hour. The reaction mixture is allowed to cool overnight (16 hours) to 130° with moderate stirring. Unreacted monomers are removed by strip-distillation at 210° with the pressure gradually reduced to 1 mm Hg. The residue is cooled to room temperature in an atmosphere of nitrogen and is clarified by filtration.

In a typical preparation, the weight of product was 1835.6 g. (a 57.3% yield); the oligomer was found to have the composition OD/DPA/MA//65.0/14.3/20.7 with a number average molecular weight of $1660 \pm 40$.

EXAMPLE XII

The Reaction of the Oligomer of Example XI with Triethylenetetramine

To a 3-liter, 4-necked, round-bottom flask fitted with a motor-driven Trubore C-stirrer, thermometer and reflux-distillation head is added 1660 g. (3.99 equiv., based on MA) of oligomer and 153.5 g. (1.05 mole) of triethylenetetramine. The mixture is heated at 130° with moderate stirring in an atmosphere of nitrogen for 8 hours, with methanol distilled upon its formation. Unreacted amine and other volatile materials are removed by vacuum strip-distillation to 155°/1 mm Hg. with intermittent sparging with nitrogen. The product is cooled in an atmosphere of nitrogen. In a typical preparation, a total of 1738 g. of product, with a base number of 67.8 and a nitrogen content of 2.86% was recovered. Analytical data indicated that 20.7% of the carbomethoxy groups from MA and 7.7% of the carboalkoxy groups from DPA were amidated.

A formulated oil containing 1.20% of the product as the sludge dispersant showed 3% top-groove fill after 409 hours in the Caterpillar 1-H test. The same oil lacking a dispersant showed 36% top-groove fill after only 240 hours.

EXAMPLE XIII

The Reaction of Ethylene Oxide with the Oligomer OD/DPA//MA/65.1/13.9/21.0 Previously Condensed with Triethylenetetramine To a 2-liter, 4-necked, round-bottom flask fitted with a motor-driven Trubore C-stirrer, thermometer, gas inlet and reflux condenser (Dewar-type) cooled with acetone-Dry Ice are added 787.6 g. (0.365 equiv. of primary amine) of the title amidated oligomer, 200 ml. of isobutyl alcohol, 100 ml. of isopropyl alcohol and 5.0 ml. of water. This oligomer is the condensation product of the oligomer OD/DPA/MA//65.1/13.9/21.0 ($\overline{M}_n$ = 1610 ± 15) and the triethylenetetramine, in which 21% of both the carbomethoxy groups from MA and carbalkoxy groups from DPA have been amidated. The mixture is heated with vigorous stirring at 70° while 18.0 g (0.406 moles) of ethylene oxide is distilled into the flask over a 45-minute period.

After holding the product mixture at 70° for 15 minutes, solvents are distilled at 100° with the pressure gradually reduced to 1 mm Hg. Quantitative reaction of ethylene oxide is observed.

A formulated oil containing 1.20% of the product as the sludge dispersant showed 6% top-groove fill after 240 hours in the Caterpillar 1-H test. The same oil lacking a dispersant showed 36% top-groove fill after 240 hours.

EXAMPLE XIV

Reaction of the Oligomer OD/DPA/MA//64.9/14.1/21.0 with Diethylenetriamine

To a 2-liter, 4-necked, round-bottom flask fitted with a motor-driven Trubore C-stirrer, thermometer, stopper and reflux-distillation head are charged 875.0 g. (2.13 equiv., based on MA) of the title oligomer and 71.4 g. (0.691 mole) of diethylenetriamine The components are heated with moderate stirring for 8 hous at 140°–142° in an atmosphere of nitrogen, with methanol distilled upon its formation. Upon expiration of the reaction time, unreacted amine and other volatile materials are removed by vacuum strip-distillation to 140° C./1.5 mm Hg. pressure with intermittent sparging with nitrogen. The product is cooled in an atmosphere of nitrogen. A total of 898.7 g. of product, with a base number of 53.3 and a nitrogen content of 2.51%, are recovered.

In a typical preparation analytical data indicated that 23.9% of the carbomethoxy groups from MA and 6.6% of the carboalkoxy groups from DPA had been amidated.

A formulated oil containing 1.20% of the product as the sludge dispersant showed 20% top-groove fill after 480 hours in the Caterpiller 1-H test. The same oil lacking a dispersant showed 36% top-groove fill after only 240 hours.

EXAMPLE XV

The Synthesis of the Oligomer: HD/DPA/MEOP//36.1/33.6/30.3

To a 2-liter, 3-necked, round-bottom flask fitted with a motor-driven Trubore C-stirrer, thermometer, a reflux condenser, 125 ml. graduated dropping addition funnel and a 1-liter graduated dropping addition funnel are added 584.5 g. (2.604 moles) of 1-hexadecene. The alkene is heated at 185° with moderate stirring in a nitrogen atmosphere. A total of 1.615 g. (0.0106 mole) of cumene hydroperoxide in 15.6 g. (0.0696 mole) of 1-hexadecene is added rapidly. Fifteen minutes later the simultaneous but separate additions of solution of 245.0 g. (0.935 mole) of dodecyl-pentadecyl acrylate and 188.4 g (0.758 mole) of 1-(methacryloxyethoxyethyl)-2-pyrrolidinone and a solution of 2.1164 g. (0.0139 mole) of cumene hydroperoxide in 20.5 g. (0.0917 mole) of 1-hexadecene are begun. The continuous addition of monomers and initiator proceeds at a constant rate. After 7.50 hours, the addition of acrylate monomers is complete, while that of initiator is 94% complete. The remaining initiator solution is added rapidly and the reaction mixture is allowed to cool to 130°–132° over the space of 16 hours with moderate stirring. The product mixture is heated at 190° for 1 hour in a nitrogen atmosphere with moderate stirring and unreacted monomers are removed by strip-distillation at 190° with the pressure gradually reduced to 3 mm Hg. The residue is cooled to ambient temperature in a nitrogen atmosphere and clarified by filtration.

In a typical preparation, the weight of product was 556.9 g. (a 52.8% yield). The oligomer, a cherry-red liquid, was found to have the composition HD/DPA/MEOP//36.1/33.6/30.3 with a number-average molcular weight of 1425 ± 25.

EXAMPLE XVI

Cooligomerization of Tetradecene-1,Lauryl Acrylate and N-(B-Acryloxyethyl)-Morpholinone-2 (BAEM)

Into a tared 500 ml., three-neck, round bottom flask, equipped with an air motor-driven stirrer, thermometer, nitrogen inlet tube, reflux condenser and a 125 ml. pressure equalized graduated addition funnel were weighted 110 g. of tetradecene-1 and 0.2 g. of dicumyl peroxide. After an initial deaeration period of approximately 20 minutes with nitrogen at room tempetature, the variable transformer controlling a heating mantle is turned on high, and the temperature of the contents of the flask raised to 150° C. A dropwise addition of the contents of the addition funnel consisting of a homogeneous solution of 84 g. of lauryl acrylate, 6 g. of BAEM above and 0.8 g. of dicumyl peroxide is then begun at such a rate that the total addition time is approximately 3 hours. The reaction mixture is kept at 150° C. with stirring and under a nitrogen blanket overnight (15 hours).

After the flask is weighed (total weight yield); 201 g.), 183.6 g. of the reaction mixture are stripped under reduced pressure (up to about 150° C. at 0.5-mm. Hg.) to give 96.2 g. of oligomer which corresponds to a weight yield of 52.4%. Analysis of the unstripped reaction mix by vapor phase chromatography and titration of the stripped oligomer using a standard perchloric acid solution in acetic acid gives the following final composition: Lauryl acrylate: tetradecene-1: BAEM 70.3:25.2:4.5 by weight. Kjeldahl nitrogen analysis gives a value of 0.39% N corresponding to 5.5% by weight of BAEM in the oligomer. Elemental analysis:

| C | H | O | N(Kj) |
|---|---|---|-------|
| 76.18 | 12.23 | 10.85 | 0.39 |

EXAMPLE XVII

Cooligomerization of Tetradecene-1, 2-Ethyl-hexyl Acrylate and N-Methacryloxyethyl-N-Methylformamide (MAMF)

Into a tared 500 ml., three-neck, round bottom flask, equipped with an air motor-driven stirrer, thermometer, nitrogen inlet tube, reflux condenser and a 125 ml. pressure equalized graduated addition funnel are weighed 110 g. of tetradecene-1 (Gulf). After deaerating with nitrogen for about 20 minutes, the tetradecene is heated to 140 ± 5° C. using a heating mantle connected to a variable transformer. Using a graduated one milliliter pipette, 0.33 ml. of a 70% solution of tertiary butyl hydroperoxide (TBHP) are added and a dropwise addition of a solution of 74 g. of 2-ethyl-hexyl acrylate, 16 g. of MAMF and 0.66 ml. of 70% TBHP is begun at such a rate that the addition is finished after about two hours. About 0.3 ml. of 70% cumene hydroperoxide (=0.1% by weight) are added and the stirring continued at 135°–140° C. overnight under nitrogen.

Total weight recovered was 199.6 g. Analysis of the unstripped reaction mix by vapor phase chromatography showed no residual 2-ethylhexyl acrylate, and oligomer yield of 62.3% and together with a Kjeldahl nitrogen (0.97%) determination on a stripped sample indicates an oligomer composition of 2-ethylhexyl acrylate:tetradecene-1:MAMF = 60.7:28.3:11.8 by weight. A number average molecular weight determination by thermal tensimetry gave an average value of 2082. Elemental analysis:

| C | H | O | N(Kj) |
|---|---|---|---|
| 73.97 | 11.27 | 13.79 | 0.97 |

EXAMPLE XVIII

Cooligomerization of Tetradecene-1, Lauryl Acrylate and 4-Pentenoic Acid

Into a tared 3000 ml., three-neck, round bottom flask, equipped with an air motor-driven stirrer, thermometer, nitrogen inlet tube, reflux condenser and a 500 ml. pressure equalized graduated addition funnel are weighed 520 g. of tetradecene-1 and 80 g. of 4-pentenoic acid.

Heating and sparging of the flask with Nitrogen are started simultaneously, after 10 minutes, with a temperature of 100° C. is reached, 1.0 ml. of tertiary butyl perbenzoate (TBPB) is added to the flask. When after an additional 10 minutes a temperature of 130° C. is reached, a slow addition of solution of 2.0 ml. of TBPB in 400 g. of lauryl acrylate is started at such a rate that the addition is finished in 3 hours. The reaction mixture is stirred at 130° C. under nitrogen for an additional 20 hours. The total weight obtained is 1000.5 g., of which 952.5 g. are stripped under reduced pressure to give 360.0 g. of distillate and 592.5 g. of oligomer which corresponds to a yield of 62.2% by weight. Analysis of an unstripped sample by vapor phase chromatography (VPC) indicates the following composition for the oligomer: lauryl acrylate: tetradecene-1: pentenoic acid = 64.2:30.2:5.6 by weight; titration of acidity by a standard KOH solution in isopropanol gave a level of 4.8% pentenoic acid in the stripped sample. Since this number is not based on differences between starting and residual concentrations as is the VPC results, it can be assumed to be more accurate. The oligomer composition is therefore, lauryl acrylate: tetradecene-1:pentenoic acid = 64.7:30.5:4.8 by weight.

EXAMPLE XIX

Cooligomerization of Tetradecene-1, 2-Ethylhexyl Acrylate and N-Vinyl pyrrolidone (NVP)

Into a tared 500 ml., three-neck, round bottom flask, equipped with an air motor-driven stirrer, thermometer, nitrogen inlet tube, reflux condenser and a 125 ml. pressure equalized graduated addition funnel were weighted 110 g. of tetradecene -1. The flask is sparged with nitrogen at room temperature for about 40 minutes, then heated to 110° C. using a heating mantle controlled by a variable transformer. A solution of 0.1 g. of benzoyl peroxide dissolved in the minimum amount of ethyl acetate is added and a dropwise addition of a solution consisting of 76 g. of 2-ethylhexyl acrylate, 14 g. of N-vinyl pyrrolidone is begun. The reaction temperature is kept between 110° C. and 115° C. and the addition finished after 3.5 hours. After the addition of 0.33 ml. of 70% tertiary butyl hydroperoxide, the reaction mixture is kept at 110° C. under nitrogen and with agitation for 15 additional hours. A total of 206 g. of material is obtained (including some ethyl acetate). Vapor phase chromatography indicates a weight yield of approximately 62.5% Kjeldahl nitrogen on a stripped sample is 1.23% by weight — this together with the VPC analysis of the residual monomers gives as a final oligomer composition: ethylhexyl acrylate: tetradecene:NVP = 61.9:28.4:9.7 by weight. The elemental analysis gave the following results:

| C | H | O | N(Kj) |
|---|---|---|---|
| 75.22 | 11.60 | 12.55 | 1.23 |

If the composition is calculated from the elemental analysis, the ethylhexyl acrylate and tetradecene percentages change to 63.9% and 26.4% respectively. A determination of the number average molecular weight by thermal tensimetry gave 4291 as the average of three measurements.

EXAMPLE XX

Reaction of 2-(5-Aminopentyl) Imidazoline with a Cooligomer of Tetradecene-1, Lauryl Acrylate and Methyl-4-Pentenoate Into a tared 500 ml., three-neck, round bottom flask, equipped with an air motor-driven stirrer, thermometer, nitrogen inlet tube and a Barrett type moisture test receiver fitted with a reflux condenser, are placed 250 g. of an oligomer of the composition lauryl acrylate:tetradecene-methyl pentenoate = 66.9:17.4:15.7 by weight which has been prepared by the same technique as described under Ex. XVIII and stripped under reduced pressure to remove unreacted monomer. Enough 2-(5-aminopentyl) imidazoline to equal one-half the moles concentration of the methyl pentenoate present is added to the flask (26.8 g.). The contents of the flask are heated to 120°–125° C. and kept at this temperature under nitrogen with stirring for about 20 hours. After the reaction mix had cooled slightly, it was poured into a 4–8 fold excess of cold, reagent grade methanol under thorough agitation. After a few minutes, the stirring is stopped and after phase separation the methanol layer is removed, using a thin glass tube attached to a suction flask which in turn is connected to a water-operated aspirator pump. To the methanolswollen oligomeric material is added an excess of reagent grade, cold methanol and the same wash cycle repeated. After a total of 4-methanol wash cycles, the oligomeric material is transferred to a rotating high vacuum type evaporator and stripped under reduced pressure to remove all traces of methanol. A Kjeldahl nitrogen determination gave 1.72% of nitrogen for the final product which is equal to 6.35% by weight of the imidazoline and therefore indicates that the reaction yield was about 66%. The C = O stretching bands appearing in the infrared scan of the final product taken as a film on a sodium chloride plate are consistent with amide-formation.

EXAMPLE XXI

Esterification of an Oligomer of Tetradecene-1, Lauryl Acrylate and 4-Pentenoic Acid with N-(B-Hydroxyethyl)-Morpholinone-2

Into a tared 500 ml., three-neck, round bottom flask, equipped with an air motor-driven stirrer, thermometer and a Barrett type moisture test receiver fitted with a reflux condenser, are placed 250 g. of the oligomer prepared in Ex. XVIII which had been stripped and the composition of which is: lauryl acrylate:tetradecene-1: pentenoic acid = 64.7:30.5:4.8 by weight. Also added to the flask are 1.2 times the molar equivalent of pentenoic acid present of N-(B-hydroxyethyl)-morpholinone-2(20.9 g.), and 54 g. of xylene in order to facilitate the removal of the water produced. Using a heating mantle controlled by a variable transformer the contents of the flask are heated to 200° C. and kept at this temperature for about 20–22 hours with agitation; approximately 2 ml. of water codistilled over during this time. The reaction mixture is stripped under reduced pressure and filtered through a pressure filtration funnel. The Kjeldahl nitrogen determination on the final oligomeric material gives a value of 0.61% which corresponds to 0.436 milliequivalents per gram; since the concentration of the acid is 0.48 milliequivalents per gram, the reaction yield amounts to $0.436/0.48 \times 100 = 91\%$.

We claim:
1. An oligomer of
    a. about 10 to about 90 weight percent of a 1-alkene, or of a mixture of 1-alkenes, all having 4 to 32 carbon atoms;
    b. about 1 to about 35% of a compound or compounds having the formula:

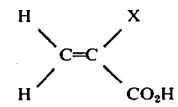

wherein X is hydrogen or a methyl group, and R is a straight or branched chain alkyl group having 8 to 34 carbon atoms, and;
    c. 1 to about 35% of a compound or compounds having the formula:

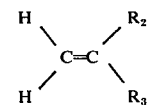

wherein $R_2$ is hydrogen or a methyl group, and $R_3$ is $(CH_2-)_nX$, wherein n is an integer ranging in value from 0 to 8, and X is any alkyl group having 1 to 4 carbon atoms,
post-reacted with an amine of the formula
    $NH_2(CH_2CH_2NH)_mH$
    wherein m is 1 to 6.

* * * * *